United States Patent [19]

Heidgen

[11] Patent Number: Plant 6,356

[45] Date of Patent: Oct. 25, 1988

[54] GERANIUM NAMED CANDY DELIGHT

[76] Inventor: Charles F. Heidgen, 821 Walnut St., Batavia, Ill. 60510

[21] Appl. No.: 782,737

[22] Filed: Oct. 1, 1985

[51] Int. Cl.[4] ..... A01H 5/00

[52] U.S. Cl. ..... Plt./68

[58] Field of Search ..... Plt./68

*Primary Examiner*—Robert E. Bagwill

[57] ABSTRACT

A new and distinct variety of geranium plant, Candy Delight, characterized by its procumbent growth habit; its large, medium to light green foliage with light zonation; its distinctive large, cotton candy pink blooms; its continuous blooming habit; and its heat tolerance.

1 Drawing Sheet

The present discovery, hereinafter referred to by the cultivar name, Candy Delight, relates to a new and distinct geranium plant.

BACKGROUND

Candy Delight is a new and improved variety which has resulted from definite breeding programs and experiments carried on by me in my greenhouses at 821 Walnut St., Batavia, Ill. Our experiments commenced in March, 1977 and are being carried on continuously. This seedling, 78S059A, is an $F_2$ seedling of Carefree Picotee, an unpatented, single-flowering zonal geranium.

Asexual propagation of Candy Delight has been accomplished from vegetative cuttings in my greenhouse in Batavia, Ill. Examination of plants so propagated has demonstrated that the combination of characteristics herein disclosed for Candy Delight are firmly fixed and retained through successive generations of asexual reproduction.

SUMMARY

The new and patentable characteristics of Candy Delight reside in its cascading growth habit, its large, cotton candy pink blossoms, its large, medium to light green foliage, its continuous flowering habit and its heat tolerance.

DESCRIPTION OF DRAWING

The photograph shows the plant and flower of a fully developed geranium of the new variety, Candy Delight.

BOTANIC DESCRIPTION

The Plant

Growth: Candy Delight is a continuous booming geranium with a somewhat upright, but cascading growth habit. The flower head (truss) is of large size and very resistant to shattering. The distinctive color of these large flowers is a light, cotton candy pink shade. Growth rate is rapid, producing a typical 10" flowering basket from four 2¼ inch plants in 10–12 weeks, using commercial standard culture. Candy Delight is Ethrel responsive.

Blooming habit: A continuous bloomer throughout the year, Candy Delight blooms well even in the heat of the summer. There may be a reduction in the number of blooms during the darker winter months. A mature 10" basket would commonly produce 9–17 heads at one time.

Inflorescence: Large-sized head, rounded, measuring 3½–4½ inches in diameter.

Foliage:

*Quantity.*—Abundant.

*Size.*—Large, 3–3¾ inches across.

*Color.*—Scheeles Green(860) with a Spinach Green (0960/3) zone. (The Royal Horticultural Society Horticultural Colour Chart).

*Texture.*—Pubescent upper and lower surfaces.

Stem: Thick, regular internodes, cascading growth habit, free branching.

Petiole: Long, 2⅔–3¾ inches long, same color as leaf.

THE FLOWER

Truss:

*Size.*—Large, 3½–4½ inches in diameter.

*Shape.*—Round, a globes as it opens.

*Number of florets.*—Variable, range from 15–35, average 19–28.

*Lasting quality.*—Average, blossoms remain 5–11 days, longer if cool and dry.

Bud: *Sepals.*—Short, pointed.

*Sepals.*—Short, pointed.

*Color.*—Rose Pink(427/2(The Royal Horticultural Society Horticultural Colour Chart).

*Form.*—Rounded, somewhat pointy.

Florets:

*Size.*—1¼–1½ inches across.

*Petalage.*—Double, 10–14 petals.

*Color.*—Neyron Rose(623/2) (The Royal Horticultural Society Horticultural Colour Chart).

Texture: Soft and fluffy.

Form: Very double flower, petals range from ⅝" to ¾" wide.

Lasting quality: Average, floret; lasts 4–8 days, truss lasts 10–12.

Behavior: When this plant is blooming, the large, soft, cotton candy pink blossoms look refreshingly cool against the medium to light green almost unzoned leaves.

Having thus disclosed my invention, I claim:

1. A new and distinct variety of geranium plant, substantially as shown and described, characterized by its procumbent growth habit; its large, medium to light green foliage with light zonation; its distinctive large, cotton candy pink blooms; its continuous blooming habit; and its heat tolerance.

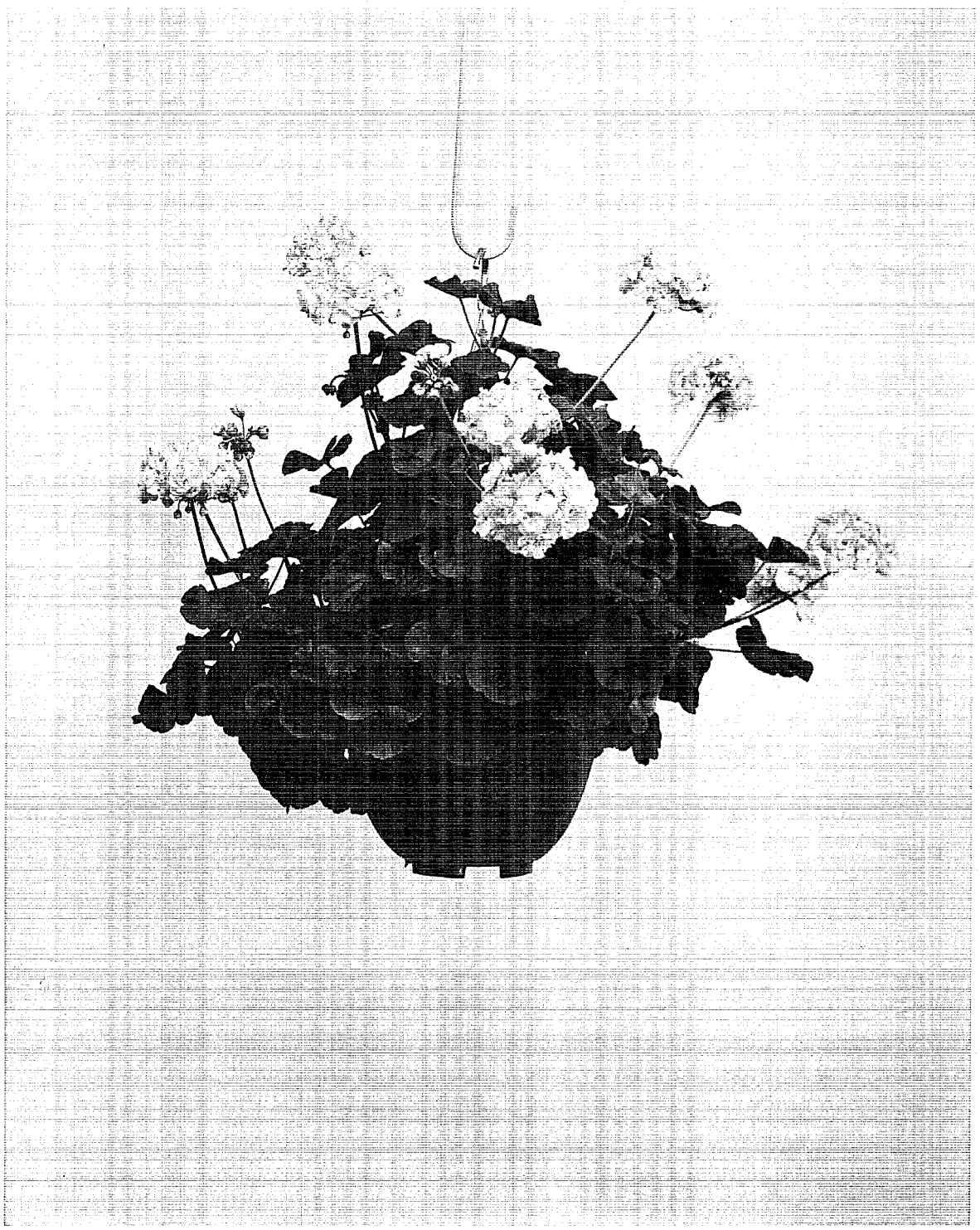

* * * * *